(12) United States Patent  (10) Patent No.: US 8,052,657 B2
Rahe-Meyer  (45) Date of Patent: Nov. 8, 2011

(54) METHOD AND DEVICES FOR SELF-DOSING A LIQUID MEDICAMENT AND FOR CONTROLLING THE DOSAGE OF THE SAME

(76) Inventor: Niels Rahe-Meyer, Hannover (DE)

( * ) Notice: Subject to any disclaimer, the term of this patent is extended or adjusted under 35 U.S.C. 154(b) by 580 days.

(21) Appl. No.: 10/484,738

(22) PCT Filed: Jul. 24, 2002

(86) PCT No.: PCT/DE02/02716
§ 371 (c)(1),
(2), (4) Date: Dec. 3, 2004

(87) PCT Pub. No.: WO03/011375
PCT Pub. Date: Feb. 13, 2003

(65) Prior Publication Data
US 2005/0119626 A1    Jun. 2, 2005

(30) Foreign Application Priority Data

Jul. 26, 2001  (DE) .................................. 101 36 081

(51) Int. Cl.
*A61M 1/00*  (2006.01)
*A61M 5/00*  (2006.01)
(52) U.S. Cl. .......................................... 604/250; 604/34
(58) Field of Classification Search .............. 604/30–35, 604/246–256
See application file for complete search history.

(56) References Cited

U.S. PATENT DOCUMENTS

| 3,450,153 | A | * | 6/1969 | Sylvan et al. | 137/486 |
| 3,832,998 | A | * | 9/1974 | Gregg | 604/65 |
| 4,121,584 | A | * | 10/1978 | Turner et al. | 604/246 |
| 4,215,689 | A | * | 8/1980 | Akiyama et al. | 604/185 |
| 4,264,020 | A | * | 4/1981 | Loiseau | 222/207 |
| 4,585,442 | A | | 4/1986 | Mannes | |
| 5,154,704 | A | * | 10/1992 | Archibald | 604/250 |

(Continued)

FOREIGN PATENT DOCUMENTS

DE    1 541 363    4/1969

(Continued)

*Primary Examiner* — Matthew F DeSanto
(74) *Attorney, Agent, or Firm* — Michael J. Striker

(57) ABSTRACT

The invention lies in the domain of medical technology and relates to a method and devices, which permit a patient to control and dose the administration of a liquid medicament from a container via a tube (4) and a catheter into the vascular system, by regulating the rate of flow of the medicament by means of a variable clamping of the tube ranging from a total block to a complete release and/or by regulating specific flow periods. To achieve this, a dosing element, preferably in the form of a mechanical rocker control switch (3), comprising a rocker (10) is put onto the tube (4), whereby the rocker (10) pivots about the rocker axis (13) pressing against the tube with its longitudinal end, by means of an adjusting coil spring (9), the flow cross-section of the tube (4) is regulated by an adjusting screw (8) on the adjusting coil spring (9) and the medicament flow through the tube (4) can also be regulated by a manually operated trigger switch (11). An electronically controlled, electrically driven radial motor (16) can be used as the dosing element in place of the rocker switch (3), said motor acting on the tube (4) and regulating the flow cross-section of the latter by means of a clamping lever (19) comprising a nose-shaped clamp (20). The method and devices for carrying out said method are illustrated by the accompanying figures.

4 Claims, 9 Drawing Sheets

U.S. PATENT DOCUMENTS 5,445,613 A * 8/1995 Orth .............................. 604/66
5,548,882 A 8/1996 Windhaus et al.

FOREIGN PATENT DOCUMENTS

| EP | 0 523 456 A1 | 1/1993 |
| EP | 0523456 * | 1/1993 |
| EP | 0 504 255 B1 | 2/1998 |
| WO | 90/07353 | 7/1990 |
| WO | 91/12834 | 9/1991 |
| WO | 93/00179 | 1/1993 |

* cited by examiner

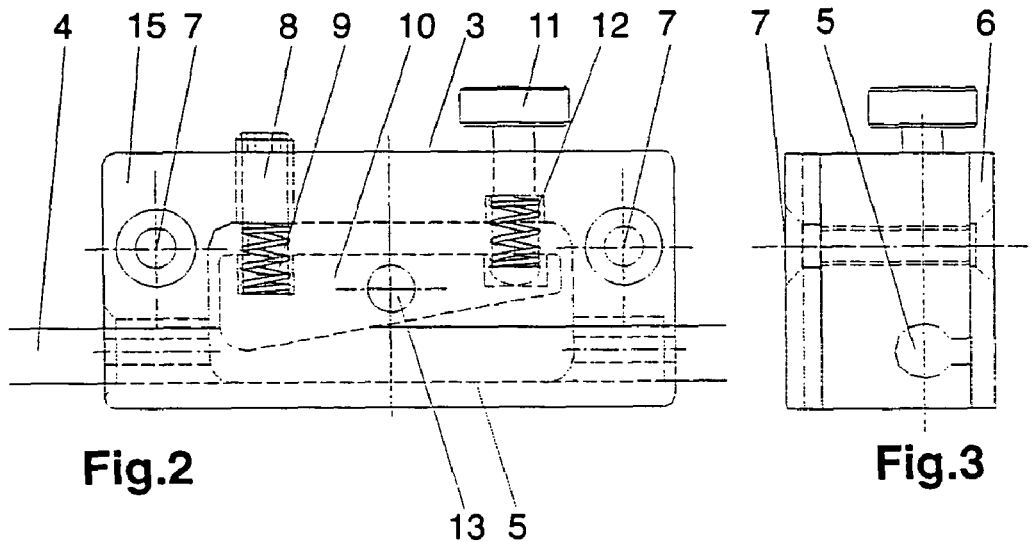
Fig.2
Fig.3
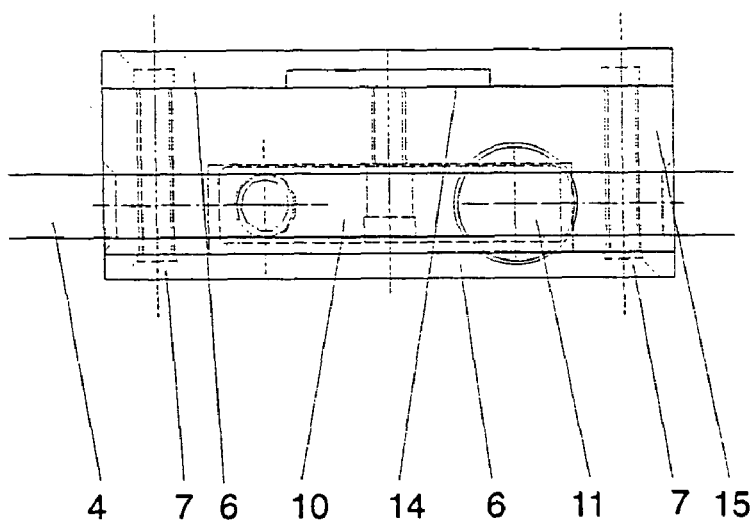
Fig.4

24 25 23  8     1  11     15     22    2 23 20   4 5

METHOD AND DEVICES FOR SELF-DOSING A LIQUID MEDICAMENT AND FOR CONTROLLING THE DOSAGE OF THE SAME

The invention is a method for the measuring of, and for the management and control of, the dosage of medications given to the vascular system, preferably intravenously. Methods and devices are known with which the time and, to a certain extent also, the dosage of the amount the medication to be administered, can be carried out by a non-medical person, namely by the patient himself. However, the known methods and devices for patient controlled-dosage have to rely on costly precision pumps and on specific, sterile, one-way materials, for example tube systems and/or medication reservoirs. When loading the medication and setting the device, the medication dosage and the concentration thereof, has to be converted to the capacity of the respective medication container, which requires an extensive introduction to the conversion tables and therefore training people to use the equipment. The high acquisition costs for the known devices, the high costs for special one-way material and the staffing requirements for the loading and setting of the equipment, through a specially trained doctor, are so high, that, especially in the area of pain therapy—particularly acute pain therapy with changing chronic pains—they are used a much less than it would be desirable.

An automatic pump device is known from EP 0 504 255 B1, namely a device for administering a remedy, controlled by the patient, which has a dosage reservoir. for the medication, with a pump device made of elastic material—which is operated by the patient—and the medication is supplied to the body through the pump effect, via a tube and a connected intravenous catheter. The liquid medication is drawn out of a separate storage container into the dosage reservoir; when the pressure is released the pump device returns to its former position and causes a partial vacuum. Apart from the requirement of a number of separate components, this pump device has the major disadvantage that it does not allow for a reliable amount of dosage of the medication, nor for the time it takes to administer, the pressure applied and the operating time, are completely dependent on the arbitrary behaviour of the patient or other operator. Apart from this, there is the danger that without the use of a check valve at the outlet of the pump device towards the far end, after releasing the pump, the liquid medication also moves back to the patient from the supply. The recommended, complementary device which determines the timing of the pump device independently of the patient operating it, is, on the one hand costly to construct and, furthermore, mostly cancels out the possibility of individual control of the pump device by the patient.

Another infusion device controlled by the patient, is also known from EP 0 592 482 B1, which has a displacement pump with a defined working volume and a separate storage for the medication, whereby, firstly, the pump has to be filled with the medication dosage through a connection tube by using a partial vacuum and then, by operating the pump, the medication is supplied to the patient from the distal end via further tubes. In addition to the separate components, a one-way/check valve is absolutely necessary, in order to avoid medication moving back to the patient from the feed-pipe, caused by the low pressure, when filling the pump from the reservoir. Thereby, the amount of the medication to be administered contained in the pump, is specifically defined through the inner diameter of the connection tube from the reservoir to the pump and, therefore, the variability of the administering of the liquid medication is decisively restricted. With this known device, according to the original intention of the invention, a detachable connection was intended to be fitted between the pump and the tube leading to the patient, to enable a faster supply of the medication.

The equipment described in EP 0 523 456 B1 is a system for the self-dosage of liquid medication, where there is also a pump, consisting of a chamber for holding the liquid medication and a push button, to be pushed down by the patient, which is connected to a separate medication bag, through a long, thin tube. The aim of the invention, according to the publication, is the arrangement of the push button, acting in combination with the spiral spring on the outside of the medication chamber, in order to reduce the height of the device. Even in this device, a one-way/check valve is necessary, which is connected to the pump outlet in the tube which runs to the patient. Furthermore, the rate of flow of the dosage of the liquid medication per se is dictated by the inner diameter of the connection tube from the medication bag to the pump—which includes the refill time of the pump chamber—so that the amount of the medication to be administered and the time interval, namely also the Bolus, can not be changed or is extremely time consuming to change.

The aim of the Invented Device is, therefore, to create a method for the dosage, and for the management and control of dosage into the vascular system—preferably intravenously—to administer liquid medication and for the implementation of the necessary devices, which simplify the known methods and devices, in such a way, that patient and/or nursing staff can use it, without special medical training, and the application of this method will be considerably more cost-effective through simplified devices.

This task is met essentially through the features of the Patent Claim 1. The devices for the implementation of the invented method are subject to the further Patent Claims.

The method and the devices are explained below, with the aid of drawings.

FIG. 2 shows: a dosage element in the form of a rocker switch in the area of the tube, from the loading unit to the infusion point, viewed from the side;

FIG. 3 shows: the dosage element as in FIG. 2, in cross-section;

FIG. 4 shows: the dosage element as in FIG. 2, viewed from above;

Figure 1:
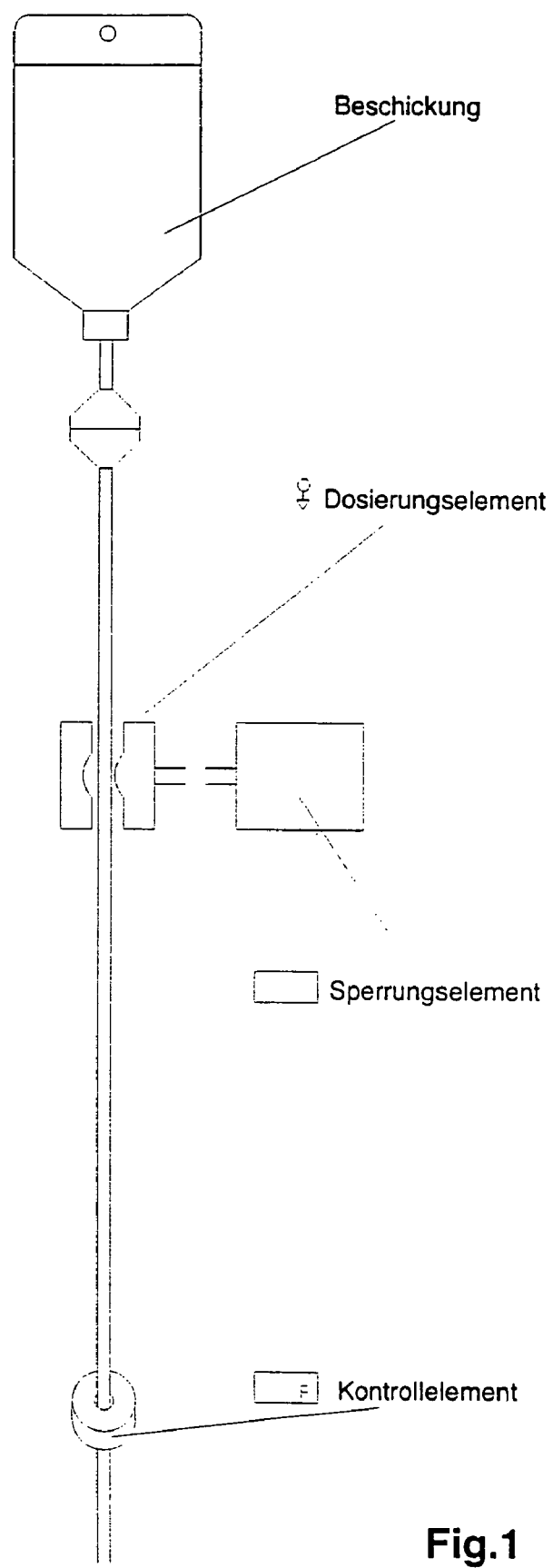
FIG. 1 shows: a diagram of the method, with illustrations of the loading, the dosage and, if need be, the cutting off and the control of the liquid medication to be administered.

With the invented method, as shown schematically in FIG. 1, the to be administered medication, for example, a pain killing drug—in liquid form—will be run from a container, where it is ready to use, via a tube (4) to a catheter and into the vascular system of the patient (this is not shown in the drawing). The amount of the medication to be administered, and the timing thereof are measured out or directed into the tube area (4), in a way either related to the amount, or to the timing or by an alternative method. To this end, the flow—meaning the amount of the medication administered during the infusion—will be varied through the clamping or releasing of the supply tube, and measured with the control element. The dosage of the medication to be administered, as well as, if needs be, an interruption to the administering of this dosage or indeed a complete stop to it, caused by cutting off the flow, is carried out according to the invented method, with a range of differently equipped dosage and cut-off elements.

In FIG. 2 to 4 there is a dosage element in the form of a mechanical rocker switch (3), shown in different versions. This rocker switch (3) has a tube socket (5), into which the tube (4) is fitted, at a point chosen and is, by means of a lid (6) with screws (7), fixed to the casing (15), so that the possibility of the tube slipping out, or unqualified removal of the tube (4) from the device, is avoided. The rocker switch (3) has a rocker (10) as a main element, around the rocker axis (13), which pushes with its long end against the tube (4), squeezing it, narrowing the flow aperture until it completely cuts off the flow. An adjustable screw spring (9) is fitted in the casing (15) of the rocker switch (3) for regulating the flow of the medication dosage into the tube, which pushes onto the aforementioned end of the rocker (10); through the appropriate adjustment of the adjusting screw (8), the rocker will be more or less pressed against the tube (4) via the adjusting screw spring (9) and changes the cross-section of the flow up to completely cutting it off. In addition to this dosage possibility, the rocker switch (3) in the example shown, has a release switch (11) on its opposite end of the rocker (10)—which is not affecting the tube (4)—which is operated manually, with an added switch spring (12), whereby the switch spring is fitted in the casing (15) and the release switch (11) has an effect onto the rocker (10) through the casing and the switch spring (12). For an additional, more arbitrary medication supply, the patient or the person treating the patient, presses the release switch (11), through which the rocker (10), via the axis (13), further or completely releases the flow in the tube (4) via the starting position, by means of the adjustable screw (8). When the switch is released again, the rocker (10), via the switch spring (12), is reverts back to its starting position.

Figure 5:
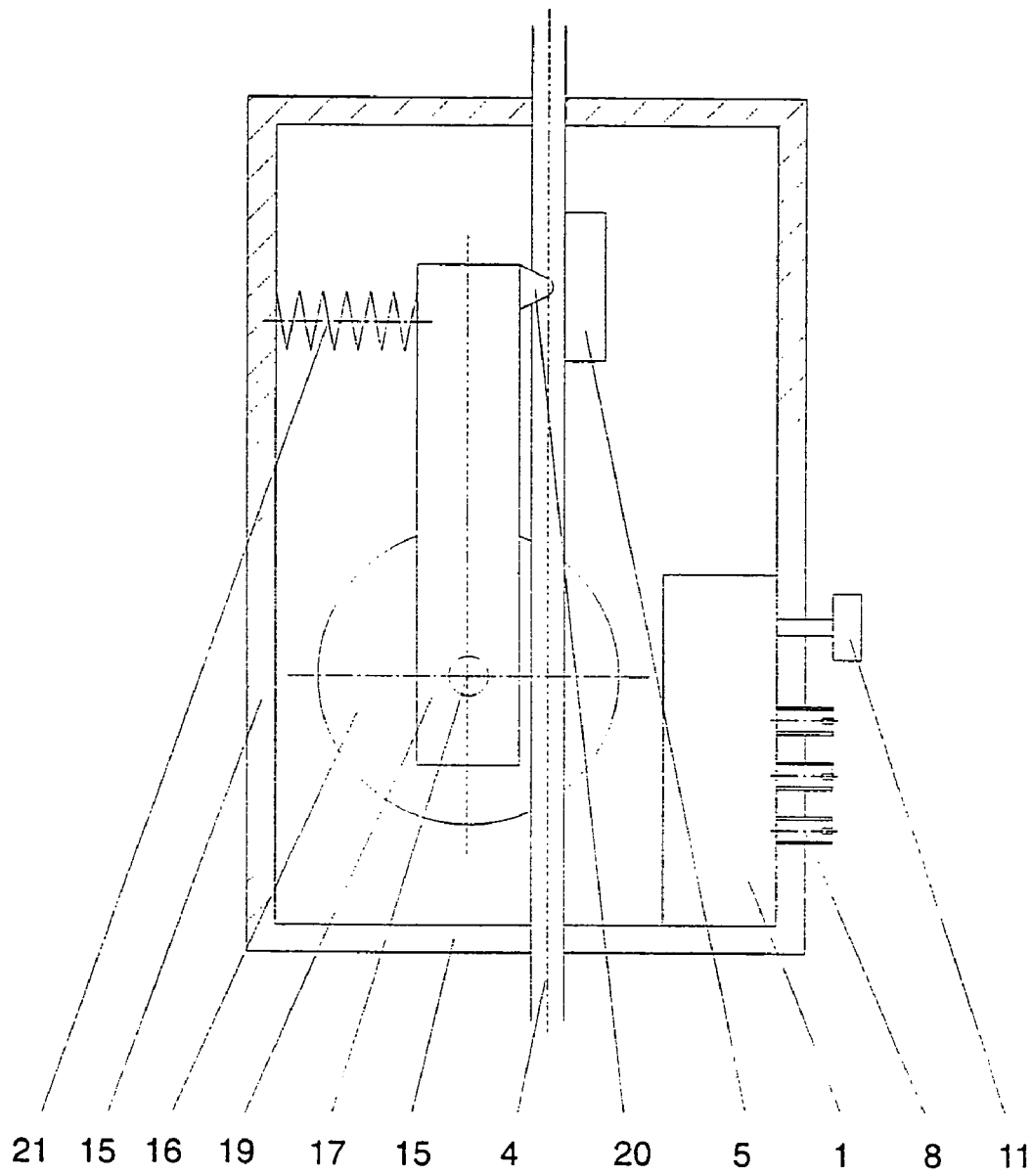
FIG. 5 shows: a dosage element in the tube area, as in FIG. 2 to 4, but with an electronically controlled radial motor for the operation of the clamp on the supply tube, viewed from the side.
Figure 6:
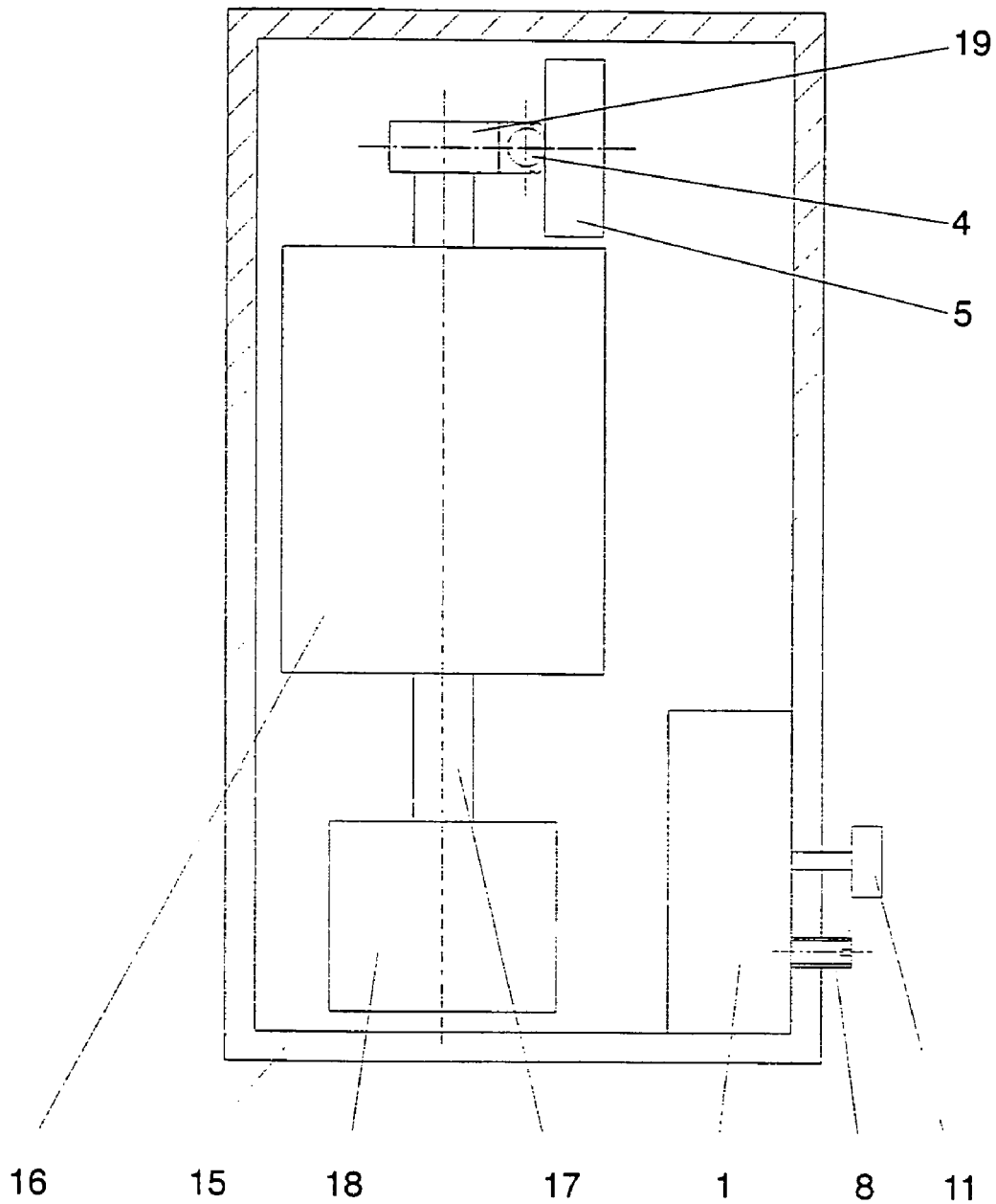
FIG. 6 shows: the dosage element as in FIG. 5, viewed from above.

Shown in FIG. 5 and 6 is another version of the dosage element with an electronically controlled, electrically driven radial motor. Firmly attached to its extended rotation axis (17) is a clamp lever (1 9), which has, on its opposite end, a nose-shaped clamp (20), which is affixed to the tube (4). The tube (4) is fitted into the tube socket (5), on its side opposite the clamp (20). The rotation axis of the motor (16), via its rotation, changes the position of the clamp lever (19) and therefore, the clamp puts pressure onto the tube (4), which therefore changes its cross-section flow up to completely cutting it off. The regulation of the motor (16) and the position of the clamp lever (19), is dictated by the electronics unit (1), which works together with a angled coding device (18) which is set on the rotation axis (17), with which the position of the motor axis (17) or the clamp (20) is being measured. In addition, there is also a release switch (11), which, when used by the patient or the nursing staff to give an extra Bolus, cancels the effect of the clamp (20). Further, in FIG. 5, in case of a fault in the functioning of the linear motor and/or of the electronics unit, a reset spring (21) is fitted onto the clamp lever (19), in the area of the clamp (20), which presses the clamp (20) against the tube (4) and thus way blocks the flow. On the electronics unit (1), the basic infusion amount is set out, as is the total maximum amount, the Bolus amounts of the medication to be administered, as well as the dead times, that is to say the time intervals, in which the release switch (11) may not be used successfully and, therefore no Bolus can be given, depending on the cross-section of the tube (4) and the catheter. In the example shown, adjustment screws (8) are provided on the electronics unit (1), for establishing these levels.

Figure 7:
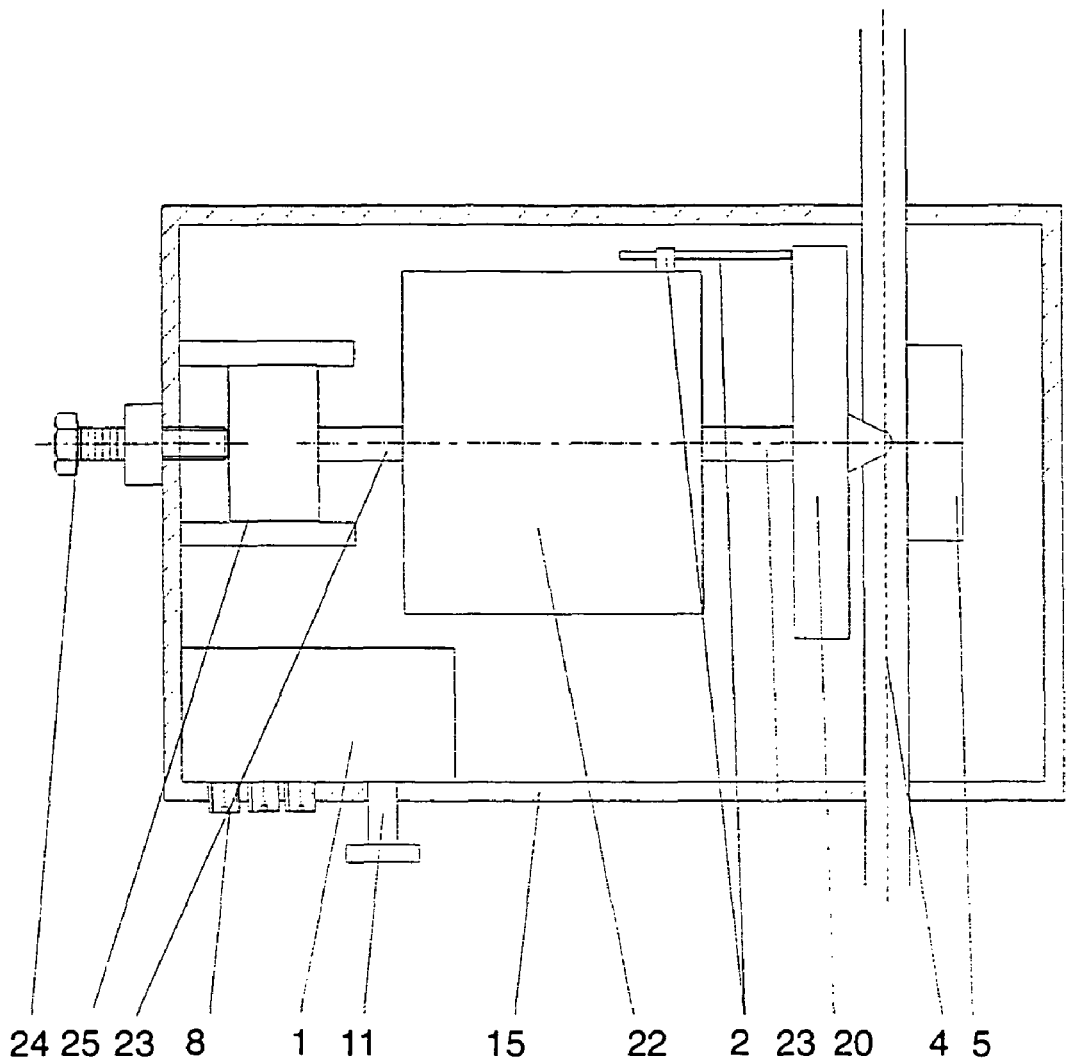
FIG. 7 shows: the dosage element in the tube area, as in FIG. 2 to 4, but with an electronically controlled linear motor for the operation of the clamp on the supply tube, viewed from the side.

In FIG. 7 there is, as an alternative version of the device for the implementation of the method, a dosage and cut off element for controlling the amount of medication to be administered, by which the clamp (20) for the tube (4) is controlled by a linear motor or a magnetic valve (22) pressing against the tube (4), whereby the linear axis (23) is firmly connected with the clamp (20) and moves, together with its nose-shaped protrusion, into the direction of the axis, according to the electronics unit (1), towards the tube (4) or away from it.

Further to this, the version of the dosage and cut-off element also shows the features of the version in FIG. 5 and 6, especially with regard to its regulation through the electronics unit (1), the adjustment screws (8) and the release switch (11). In addition, a screw (24) is fitted on the linear axis (23), on its end, facing away from the clamp (20); this screw is calibrated and enables the clamp (20) to be removed from tube the (4), to set the amount of the infusion. The position of the clamp (20) can also be measured with a linear length meter (2).

Figure 8:
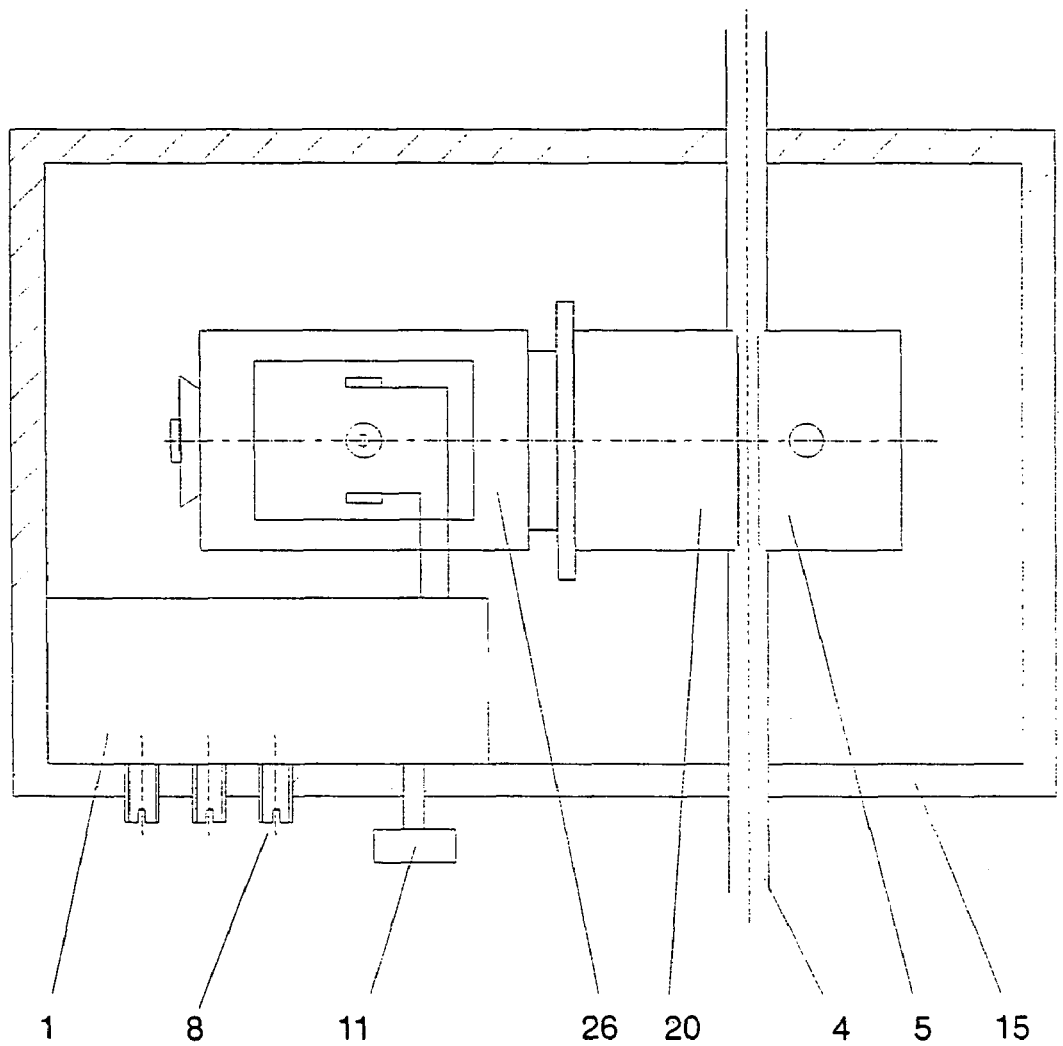
FIG. 8 shows: the dosage element in the tube area, as in FIG. 2 to 4, but with an electronically controlled valve, for changing the flow through the tube, viewed from the side.

A further version of the dosage and cut-off element is shown in FIG. 8, by using a tube valve. The tube (4) runs in a channel, which is adapted to accommodate it, within the clamp (20) for the magnetic valve (26). The magnetic valve (26) is connected to the electronics unit (1), together with the adjusting screws (8) and the release switch (11), as in the versions described above, and is controlled through these. When the tube valve (26) is in its resting position, the tube is completely clamped off, so that the medication flow is stopped. When activating the tube valve (26), the lumen of the tube is released and therefore the flow, in accordance with the set levels as controlled by the electronics unit (1). The remaining functions correspond to the versions described above. By automatically releasing small Bolus amounts of the liquid medication at intervals, they add up to a constant quantity of the basis infusion, which can be varied through changes in the interval times and the Bolus quantities.

Figure 9:
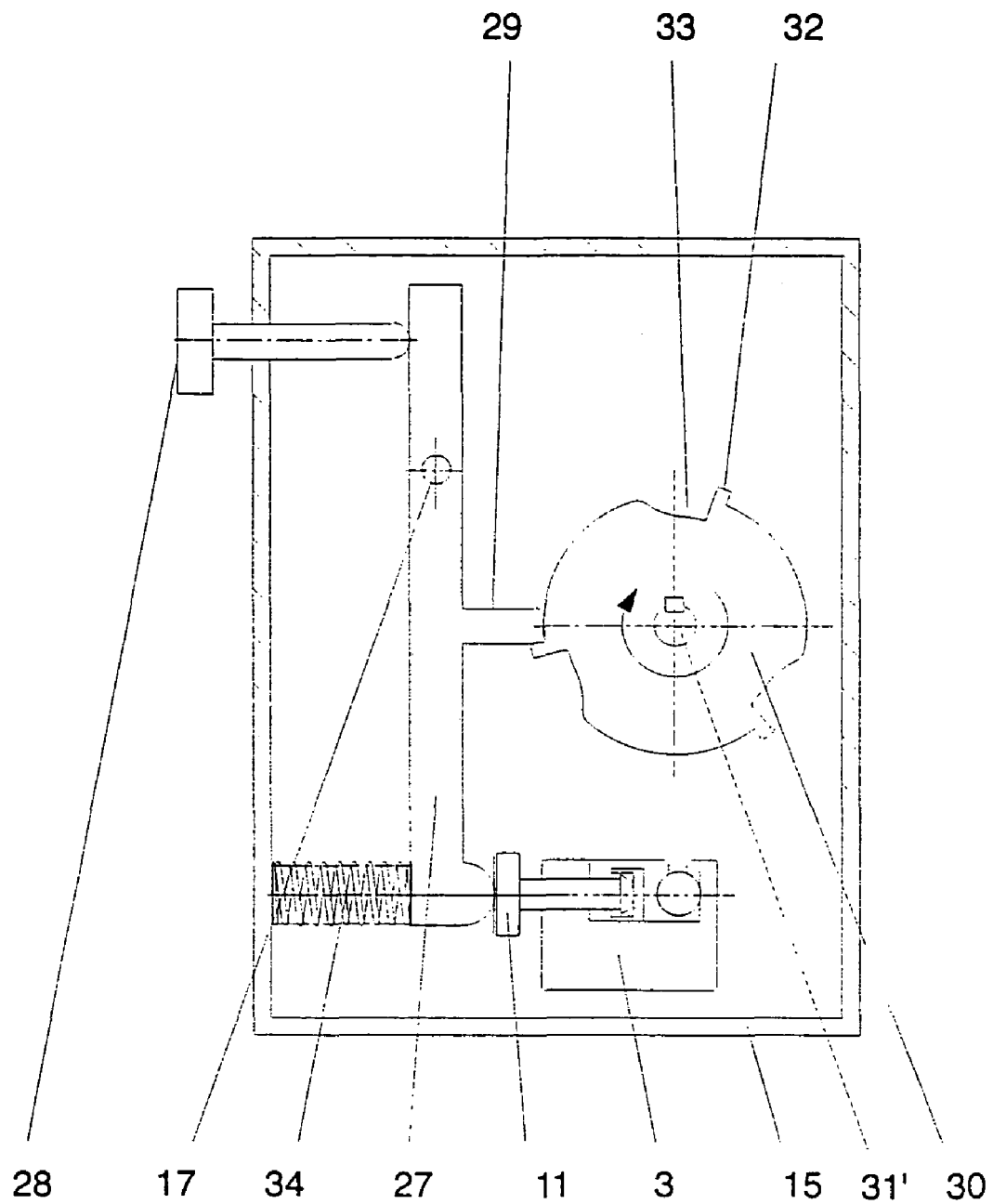
FIG. 9 shows: the dosage element with the rocker switch as in FIG. 2 to 4, controlled by a clockwork element, for the cutting off of the tube flow, in cross-section.
Figure 10:
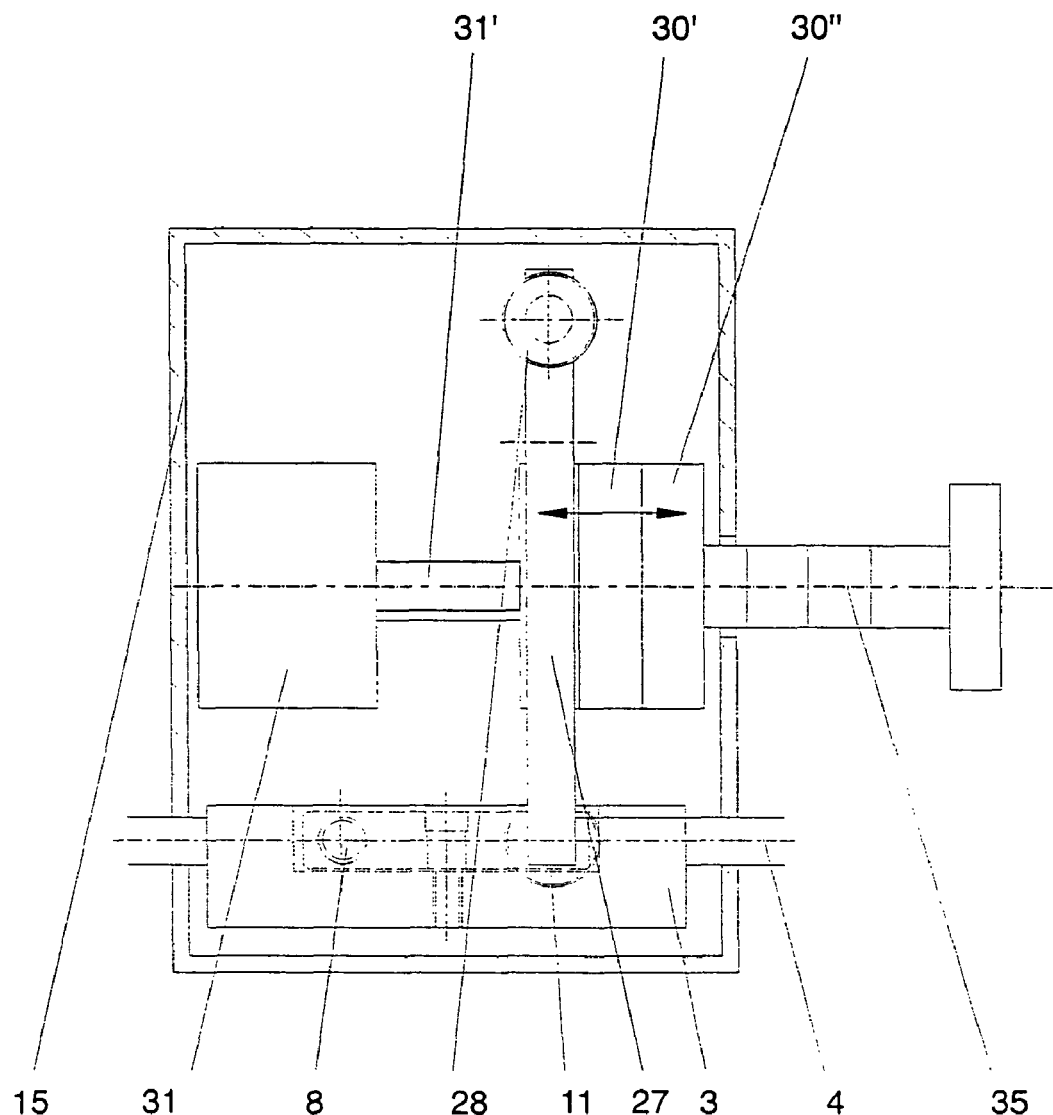
FIG. 10 shows: the dosage element with cut-off element, as in FIG. 9, in cross-section.

Shown in FIG. 9 and 10 is a time controlled cut-off or interruption element, for the interruption of the flow of the liquid medication through the tube (4), over defined time intervals, which works together with the dosage device, with the rocker switch (3), as in FIG. 2 to 4. A notched lever (27) is thereby fitted in such a way, that one of its ends sits on the pressure area of the release switch (11) for the rocker switch (3). The notched lever (27) rests in the area opposite its far end and rotates around an axle (17). Between this axle (17) and the end, the release switch (11) is fitted to the notched lever (27), which has a nose-shaped protrusion (29), which firmly grips the outer rim of the notched disc (30). This notched disc sits on an axle (31 '), running parallel to the axle (17) and also parallel to the tube (4), and is driven clockwise by a clockwork mechanism (31) on the same axle. The notched disc (30) has one or more indentations in the form of notched disc slots (33) and has, clockwise, in front of each these, a notched disc lip (32), which protrudes over the disc rim. The notched lever

(27) is fitted with a pressure spring (34) on its rear side, in the area where it slots into the release switch (11), which exerts pressure, via the lever, onto the release switch. The notched lever nose (29) sits on top of the notched disc (30) and stops the release switch (11) from being pushed into the rocker switch (3) by the pressure spring (34) and therefore stops the opening of the clamp on the tube supply (4) through the adjusting screw (8) and the adjusting screw spring (9).

The notched lever stays in this position until the notched disc lip (32) strikes the notched lever nose (29), via the rotation of the notched disc (30). By pushing down a release switch (28) for the notched lever (27)—which grips the opposite end of the notched lever (27) in front of its axle (17) and the notched lever nose (29)—the notched lever can be raised in such a way, that the notched lever nose (29) is no longer blocked by the notched disc lip (30), when the notched disc (30) is further rotated on its axle (17). When the notched disc (30) is advanced by the clockwork mechanism (31), the notched lever nose (29) moves into the area of the notched disc slot (33), so that the notched lever (27)—after the release of the release switch (28)—can push down the release switch (11), through the pressure spring (34), and thus, completely open the supply tube for giving the Bolus. When the notched disc (30) is further rotated, the notched lever nose (29) moves out of the slot once again, as a result of which, the notched lever (27) counteracts the power of the pressure spring (34). At the same time, the operation of the release switch (28) is prevented and thus, rules out the dispensing of a Bolus. By changing the speed of the rotation of the notched disc (30), via the clockwork mechanism (31) or the use of other notched discs (30', 30") with a different number, shape or changed positioning of the notched disc slots (33) or by means of an adjustment to the notched disc (35), the time intervals of the interruptions to the medication supply can be changed. By altering the lengths of the notched disc slots (33), the duration of the opening of the complete lumen of the tube (4)—for the dispensing of the Bolus—can be changed.

All versions of the dosage and cut-off element are arranged in a casing (15).

The control of the administered amount of the liquid medication is carried out in ways known or, alternatively, also in a cumulative manner through a drop counter, a flow measurer or a scale, which are positioned in the area of the tube (4), in front of the infusion unit. A linear potentiometer on the dosage element can also be used for this, or the patient's oxygen saturation of the blood can be measured.

Figures 11, 12:
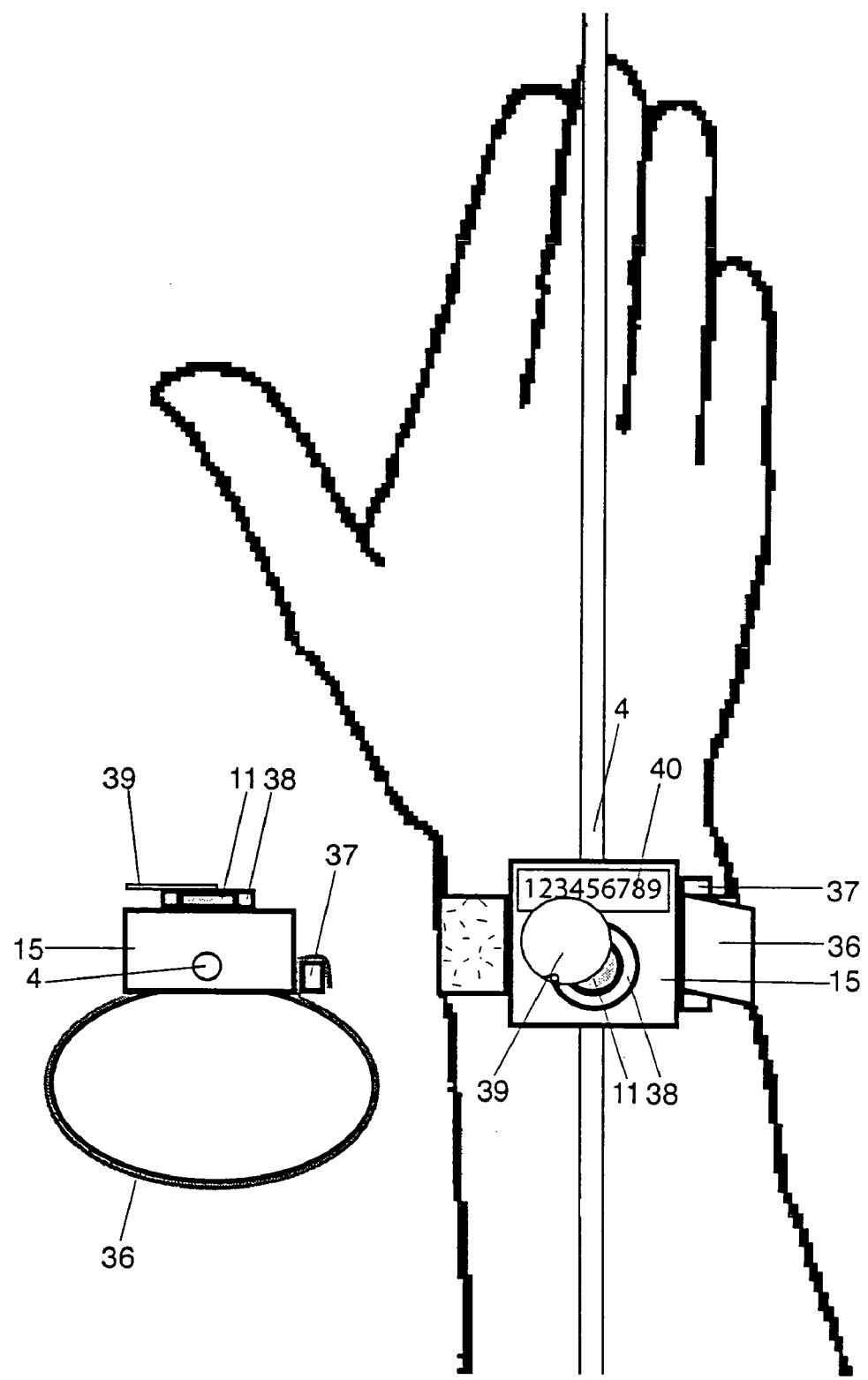
FIG. 11 shows: a mounting for the dosage element, as in FIG. 2 to 10, for the securing of the human arm, viewed from above.
FIG. 12 shows: the mounting for the dosage element, as in FIG. 11, in cross-section.

To secure the release switch (11) against accidental use, it is sunken into a protective ring (38) and covered by a lid with a spring (39), as seen in FIG. 11.

For the secure mounting of the dosage and cut-off element, when using the method as described, these elements are each provided with a fastener (36) together with a clasp (37), on their casing (15), with which the elements can be fitted to the arm of the patient, to the infusion stand, to the bar over the bed or to another suitable place, in such a way, that the release switch (11) is safely within the patients reach (FIG. 11 and 12).

When the version is in use, a display (40) is fitted in the casing (15), also apparent in FIG. 11, on which, for example, the number of the successful/unsuccessful times that the release switch (11) has been used or other data of the patients' history, can be displayed.

The method according to the invention and the described devices for its implementation, make possible the external management of the medication dosage and the speed of administering the medication. A defined basis infusion speed is made possible, as well as the administering of defined Boluses/Boli. Furthermore, the setting of time intervals is made possible—for the cut-out of the release of the medication or the administering of the Bolus, and the setting of the limitations on the amount of the medication administering for particular intervals.

The method can hereby, using traditional infusion or transfusion systems, be used for the administering of medication, whereby the medication, for example, pain killers, can be added to the infusion solution. The method does not need elaborate transport systems, for example, in the form of a precision pump, separate reservoir containers with connection leads or a one-way/check valve. It can be implemented without additional, specialist, one-way materials. Not withstanding this, the variability of the amount and the timing, as well as the intervals for the administering of the medication, is increased. It is possible with this method, to design the technical aspects of the devices in such a simple way, that, in comparison to known patient-controlled dosage systems, only a fraction of the manufacturing costs are incurred, and that a strongly simplified operational concept can be used, that allows medical staff, who are not especially trained, to load and prepare the devices and set the basic settings. The method described, abstains from using precision drives and consciously accepts, with regard to known devices, the possibility of a less precise dosage.

Therefore, it is especially useable in the management of acute pain, for example, with post-operative pains, where the strength of the pain is variable and not predictable and changes immensely in its course, and which makes a precise, patient-suitable, basic setting anyway impossible.

When using the recommended versions of the dosage elements with electronic controls, a setting with many cut-off and control levels is possible, depending on the usage, or, a simpler setting for the administering of the medication is possible, with fewer levels, which is tailored to the special requirements of the individual patient. The settings, up-to-the-minute consumption levels of the medication and the successful or unsuccessful—because of the cut—use of the release switch, are all visible on display.

The invention claimed is:

1. A device for a self-dosage and management of an administered dosage of a liquid medication in a liquid form into a vascular system of a patient by using a conventional infusion or transfusion system from a container, comprising a tube leading to a catheter; a dosage element acting on said tube directly so as to change a flow aperture of said tube and thereby to change the administered dosage of the liquid medication; and a manually actuateable release element cooperateable with said dosage element, so that said manually actuateable release element at least partially releases the action of the dosage element on said tube without acting directly on said tube so that the flow aperture of said tube can be closed, partially open, or completely open to change a quantity and a time of a supply of the liquid medication including time periods with a full closure of said tube and without a pump, wherein said tube extends in a predetermined direction, wherein said dosage element includes a rocker having two ends spaced from one another in said direction with one end pressable against said tube to change the flow aperture and another end associated with said release element; and further comprising two springs including an adjustable spring cooperating with said one end of said rocker so that said one end of said rocker is pressed more or less against said tube via said adjustable spring, and a switch spring cooperating with the other end of said rocker to revert said other end of said rocker to its starting position after said release element acted on said dosage element, said two springs extending in a same direction transversely to said predetermined direction of extension of said tube.

2. A device for a self-dosage and management of an administered dosage of a liquid medication in a liquid form into a vascular system of a patient by using a conventional infusion or transfusion system from a container, comprising:

a tube leading to a catheter;

a dosage element including a clamp lever having two ends spaced from one another in said direction with one end having a nose-shaped clamp element pressed against said tube to change a flow aperture, a reset spring fitted onto said clamp lever in an area of the clamp, and a motor having an axle to which another end of said clamp lever is attached for joint rotation therewith;

a manually actuateable release element cooperateable with said dosage element, so that said manually actuateable release element at least partially releases the action of the dosage element on said tube without acting directly on said tube so that the flow aperture of said tube can be closed, partially open, or completely open to change a quantity and a time of a supply of the liquid medication including time periods with a full closure of said tube and without a pump;

an electronic unit for regulating said motor and thereby the position of said clamp lever;

an angled coding device arranged on said axle and cooperating with said electronic unit for measuring a position of said axle or said clamp lever; and wherein said dosage element acts on said tube directly so as to change the flow aperture of said tube and thereby to change the administered dosage of the liquid medication, said tube at a side which is opposite to said another end of the clamp element being fitted into a tube socket, wherein said motor is adapted to change a position of said clamp lever during rotation of said axle to act on said tube with said nose-shaped element of said clamp lever so as to change a cross-section of the flow aperture, wherein said release element is configured for manually acting on said clamp lever for releasing action of said clamp element, and wherein the reset spring acts on said one end of said clamp lever to press the clamp against the tube.

3. A device as defined in claim 2; and further comprising an electronic unit for regulating said motor and thereby the position of said clamp lever.

4. A device as defined in claim 3, wherein said electronic unit is provided with adjustment screws for dosing the medication and setting an amount and/or a time limitation for release of the medication.

* * * * *